(12) United States Patent
Kwon et al.

(10) Patent No.: US 10,588,906 B2
(45) Date of Patent: Mar. 17, 2020

(54) METHOD OF PREVENTING HAIR LOSS OR PROMOTING HAIR GROWTH BY USING PHOSPHODIESTERASE 3 INHIBITOR

(71) Applicant: SEOUL NATIONAL UNIVERSITY HOSPITAL, Seoul (KR)

(72) Inventors: Ohsang Kwon, Seoul (KR); Hye-In Choi, Seoul (KR); Seong Jin Jo, Seoul (KR); Kyu Han Kim, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 20 days.

(21) Appl. No.: 16/045,014

(22) Filed: Jul. 25, 2018

(65) Prior Publication Data
US 2019/0046528 A1 Feb. 14, 2019

(30) Foreign Application Priority Data

Aug. 8, 2017 (KR) .................. 10-2017-0100411
Apr. 20, 2018 (KR) .................. 10-2018-0046279

(51) Int. Cl.
| | |
|---|---|
| *A61P 17/14* | (2006.01) |
| *A61K 31/41* | (2006.01) |
| *A61K 31/425* | (2006.01) |
| *A61K 31/47* | (2006.01) |
| *A61K 31/4704* | (2006.01) |
| *A61K 31/505* | (2006.01) |
| *A61Q 7/00* | (2006.01) |
| *A61K 8/49* | (2006.01) |
| *A61K 31/047* | (2006.01) |

(52) U.S. Cl.
CPC ............ *A61K 31/505* (2013.01); *A61K 8/494* (2013.01); *A61K 8/4926* (2013.01); *A61P 17/14* (2018.01); *A61Q 7/00* (2013.01); *A61K 8/4953* (2013.01); *A61K 31/047* (2013.01)

(58) Field of Classification Search
CPC .... A61K 31/41; A61K 31/4425; A61K 31/47; A61K 31/4704; A61P 17/14
See application file for complete search history.

(56) References Cited

U.S. PATENT DOCUMENTS

| | | | | |
|---|---|---|---|---|
| 5,141,936 | A | * 8/1992 | Rupp ................... | A61K 8/4953 |
| | | | | 514/227.8 |
| 2013/0267558 | A1 * | 10/2013 | Kim ....................... | A61K 31/41 |
| | | | | 514/312 |

OTHER PUBLICATIONS

AGRYLIN®: Anagrelide HCl Capsules. Reference ID:3449753. Manufactured for Shire US Inc., 725 Chesterbrook Blvd., Wayne, PA 19087, USA 1-800-828-2088 © 2014 Shire US Inc. Rev. Feb. 2014. (Year: 2014).*
Kim et al., "The effect of cilostazol on hair growth: A type of drug repositioning for the treatment of alopecia with the mechanism of vasodilatation", The 27th Annual Meeting of the Korean Society for Investigative Dermatology / Poster Presentations, HP-11, published on Mar. 24, 2017.
Kim et al., "The effect of cilostazol on hair growth: A novel therapeutic option for the treatment of hair loss", Society for Investigative Dermatology / Poster Presentations, Abstract 873, published on Apr. 26, 2017.
Choi et al., "The effect of cilostazol, a phosphodiesterase 3 (PDE3) inhibitor, on human hair growth with the dual promoting mechanisms" in Journal of Dermatological Science, published on Apr. 11, 2018.

* cited by examiner

*Primary Examiner* — Jeffrey S Lundgren
*Assistant Examiner* — Chris E Simmons
(74) *Attorney, Agent, or Firm* — Vorys, Sater, Seymour & Pease LLP; Mih Suhn Koh

(57) ABSTRACT

Provided herein is a method of preventing hair loss or promoting hair growth, the method including administering an effective amount of a PDE 3 inhibitor. More particularly, when the method of the present disclosure is used, an excellent hair loss prevention or hair growth promotion effect is obtained by inhibiting the activity of PDE 3.

5 Claims, 11 Drawing Sheets

METHOD OF PREVENTING HAIR LOSS OR PROMOTING HAIR GROWTH BY USING PHOSPHODIESTERASE 3 INHIBITOR

STATEMENT REGARDING GOVERNMENT RIGHTS

The present invention was undertaken with the support of "A study of controlling mechanism on folliculoneogenesis and hair growth through the regulation of phosphodiesterase" No. 2016R1D1A1B03931130 grant funded by the National Research Foundation of Korea.

CROSS-REFERENCE TO RELATED APPLICATION

This application claims priority to and the benefit of Korean Patent Application No. 10-2017-0100411, filed on Aug. 8, 2017 and Korean Patent Application No. 10-2018-0046279, filed on Apr. 20, 2018, the disclosure of which is incorporated herein by reference in its entirety.

BACKGROUND

1. Field

The present disclosure relates to a method of preventing hair loss or promoting hair growth by using a phosphodiesterase 3 (PDE 3) inhibitor as an active ingredient.

2. Discussion of Related Art

Human hair grows and is maintained and removed through three stages, i.e., anagen, catagen, and telogen phases, according to the growth cycle. In the anagen phase where the hair continue to grow, it is known that for adults, the hair grows an average of about 0.3 mm per day and by about 1 cm a month, and the anagen phase lasts about 5 years to about 8 years. Generally, after the anagen phase, the hair is removed through the catagen phase of about 3 weeks, and the telogen phase of an average of 3 months, and a reason why the length of the human hair varies according to each site is that the duration of the anagen phase, which is an intrinsic characteristic of a hair follicle, is different.

The hair is formed in hair follicles, which are very complex organs consisting of an inner root sheath, an outer root sheath, a hair shaft, hair matrix cells, and the like. In particular, hair dermal papilla cells (hDPCs) are directly associated with hair follicle-forming ability, and thus play a key role in hair follicle formation, and therefore, in the absence of hDPCs or when hDPCs cannot function, hDPCs and epidermal cells cannot appropriately interact with each other, resulting in non-formation of hair follicles.

Hair loss refers to the partial or total loss of hair from the part of the body where hair normally exists, and it is known that hair loss is caused by intricately involved factors such as genetic causes, and physical and mental stresses such as male hormone action, endocrine diseases, undernutrition, drug use, labor, pyrexia, surgery, and the like. Recently, the female hair loss population has tended to increase due to changes in dietary life and an increase in stresses by the social environment and the like as well as the male hair loss population, and the number of people suffering from the abnormal symptoms of the scalp and the hair is gradually increasing and the age of the population is also getting younger.

Domestically and internationally, research on anti-hair loss agents and hair growth promoters has been accelerating and a variety of products have been developed, but there are no anti-hair loss agents which have excellent efficacy and are safe for the human body. Although external application products including minoxidil preparations made in the U.S.A, herbal medicine extracts made in Japan, and the like are being currently developed as a hair restorer or a hair growth promoter, it is still early to achieve a hair loss prevention function and a hair growth function in terms of efficacy thereof.

Currently, there are only 5a reductase inhibitors such as finasteride and dutasteride as effective therapeutics for male hair loss, but their therapeutic effects vary from person to person, and existing hair loss therapeutic agents approved by the US FDA are drugs developed mostly for male hair loss, and thus there is a limitation in addressing female hair loss and rather, there is a possibility of causing side effects in females. Therefore, there is a very urgent need to research a novel anti-hair loss agent and hair growth promoter which can be proved to be safe and effective in both men and women.

Meanwhile, a phosphodiesterase 3 (PDE 3) inhibitor increases the concentration of cyclic adenosine monophosphate (cAMP), which is an intracellular secondary messenger, by inhibiting the action of the 3rd subtype enzyme among 10 or more phosphodiesterase enzyme subtypes, thereby affecting various gene transcription processes, protein expression regulation, and various important cAMP-mediated physiological processes, is used as a therapeutic agent of diseases such as acute heart failure, cardiogenic shock, intermittent claudication, and the like, and is currently used as a target for inhibiting various pharmacological mechanisms. However, the effect of the PDE 3 inhibitor on hair loss prevention or hair growth promotion has not yet been reported.

SUMMARY

To address the above-described existing problems, as a result of having intensively studying a method of promoting hair growth using PDE 3 inhibitors including cilostazol which has been proven to be safe, the inventors of the present disclosure verified that the PDE 3 inhibitors promote the proliferation of hair dermal papilla cells (hDPCs) derived from human hair follicles, which are core cells in hair follicle formation and hair growth, and promote hair growth in hair follicle organic culture and an anagen induction test using an animal, and thus have an excellent effect of preventing hair loss or promoting hair growth, and completed the present disclosure based on these findings.

Therefore, the present disclosure relates to a method of preventing hair loss or promoting hair growth by using a PDE 3 inhibitor as an active ingredient, and more particularly, to a method of preventing hair loss or promoting hair growth by administering, to a subject, an effective amount of a PDE 3 inhibitor having an effect of preventing hair loss or promoting hair growth.

However, technical problems to be solved by the present disclosure are not limited to the above-described technical problems, and other unmentioned technical problems will become apparent from the following description to those of ordinary skill in the art.

According to an aspect of an embodiment, there is provided a method of preventing hair loss or promoting hair growth, the method including administering an effective amount of a phosphodiesterase 3 (PDE 3) inhibitor to a subject.

The PDE 3 inhibitor may be cilostazole, amrinone (inamrinone), adibendan, anagrelide, benafentrine, bucladesine, carbazeran, cilomilast, cilostamide, enoxamone, fenspiride HCl, 1-cyclopropyl-1-[(1R,2R)-2-hydroxycyclohexyl]-3-[3-[(2-oxo-1H-quinolin-6-yl)oxy]propyl]urea (K-134), 7-[2-[4-(2-chlorophenyl)piperazin-1-yl]ethyl]-1,3-dimethylpurine-2,6-dione (KMUP-1), luteolin, 8-amino-3,7 dihydro-7-(2-methoxyethyl)-1,3-dimethyl-1H-purine-2,6-dione (MKS492), meribendan, milrinone, olprinone, 1-cyclooctyl-1-[(1R,2R)-2-hydroxycyclohexyl]-3-[3-[(2-oxo-1H-quinolin-6-yl)oxy]propyl]urea (OPC-33540), 3-(5,6-dimethoxy-1-benzothiophene-2-yl)-4-methyl-4,5-dihydro-1H-pyridazin-6-one (ORG 9935), parogrelil, pimobendan, pumafentrine, quazinone, 2-[9,10-dimethoxy-4-oxo-2-(2,4,6-trimethylphenyl)imino-6,7-dihydropyrimido[6,1-a]isoquinolin-3-yl]ethylurea (RPL-554), siguazodan, salbutamol, trequinsin, vesnarinone, zardaverine, or the like, but the PDE 3 inhibitor is not limited to the above examples as long as it is an inhibitor capable of inhibiting the mechanism and/or activity of PDE 3.

In one embodiment, in the method, the PDE 3 inhibitor may be administered at a concentration of about 0.0001 mM to about 50 mM, but the concentration of the PDE 3 inhibitor is not limited thereto as long as it is a concentration that causes no harm to a human body.

In another embodiment, the PDE 3 inhibitor may be used for the prevention or treatment of alopecia. In particular, the alopecia may be any one or more selected from the group consisting of alopecia areata, androgenetic alopecia, telogen effluvium, traumatic alopecia, trichotillomania, pressure alopecia, anagen effluvium, nasal alopecia, alopecia syphilitica, alopecia seborrheica, symptomatic alopecia, cicatricial alopecia, and congenital alopecia, but the present disclosure is not limited thereto.

In addition, the PDE 3 inhibitor according to the present disclosure may be administered as a pharmaceutical composition, a cosmetic composition, a preparation for external application to the skin, a quasi-drug composition, or the like to a subject.

The preparation for external application to the skin may be any one or more selected from the group consisting of a scalp treatment agent, soap, hair tonic, a shampoo, a rinse, a hair pack, a hair gel, a lotion, a conditioner, hair oil, mousse, a cream, a solid preparation, a liquid preparation, an emulsion, a dispersion, micelles, liposomes, an ointment, a toner, essence, a patch, and an aerosol, but the present disclosure is not limited to the above examples.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 3 illustrates ex vivo hair follicle organ culture test results according to an embodiment, wherein

FIG. 5 illustrates analysis results of the formation of anagen hair follicles due to cilostazol according to an embodiment, wherein

FIG. 7 illustrates verification results of the effect of cilostazol on angiogenesis around hair follicles, according to an embodiment, wherein

DETAILED DESCRIPTION OF EXEMPLARY EMBODIMENTS

Figure 1:
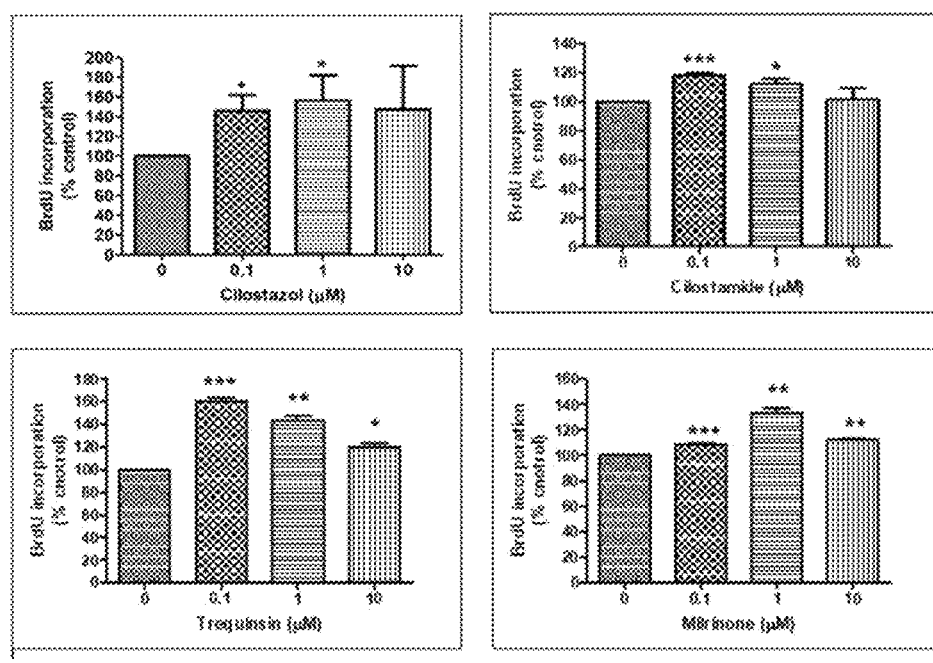
FIG. 1 illustrates graphs showing verification results of the effects of phosphodiesterase 3 (PDE 3) inhibitors on cell proliferation by treating human hair dermal papilla cells with cilostazol, cilostamide, trequinsin, or milrinone and performing a BrdU assay thereon, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As result of having conducted intensive studies to develop drugs proven to have less side effects and objective and reproducible effects on alopecia, the inventors of the present disclosure verified that a phosphodiesterase 3 (PDE 3) inhibitor had an excellent effect on hair loss prevention or hair growth by promoting hair growth, and thus completed the present disclosure based on the findings.

Hereinafter, the present disclosure will be described in detail.

The present disclosure relates to a method of preventing hair loss or promoting hair growth by using a PDE 3 inhibitor as an active ingredient, and more particularly, to a method of preventing hair loss or promoting hair growth, the method including administering an effective amount of a PDE 3 inhibitor having an effect of preventing hair loss or promoting hair growth to a subject, and thus the method may be used for the prevention or treatment of alopecia.

In one embodiment, to evaluate the effect of PDE on the proliferation of hair follicle cells, human hair follicle-derived hair dermal papilla cells (hDPCs) were treated with cilostazol, cilostamide, trequinsin, or milrinone, which are PDE 3 inhibitors, and then subjected to BrdU and western blotting (see Examples 1 and 2).

In another embodiment, to evaluate the effect of cilostazol on the growth of human hair follicles, an ex vivo hair follicle organic culture test was performed, and to verify the proliferation of cultured hair follicle cells through the test, immunofluorescence staining was performed using an antibody against Ki-67, which is a cell division marker (see Example 3).

In another embodiment, the effect of cilostazol on hair growth was identified using a C57BL/6 mouse model, skin tissue from which anagen hairs grew was fixed with paraffin and stained with hematoxylin and eosin to conduct a histological examination, and an anagen induction degree and skin thickness were measured (see Example 4).

In another embodiment, to identify the effect of cilostazol on a mitogen-activated protein kinase (MAPK)-associated signaling pathway, which is a cell proliferation-associated signaling pathway, in mouse tissue, western blotting was performed using mouse skin tissue (see Example 5).

In another embodiment, to identify the effect of cilostazol on angiogenesis around hair follicles, immunofluorescence staining with CD31, which is a blood vessel marker protein, was performed (see Example 6).

The term "alopecia" as used herein refers to hair loss in an area where hair normally exists, and generally refers to the loss of terminal hair (thick and black hair) of the scalp. Unlike vellus hair, which has no color and is thin, when terminal hair is lost, aesthetic problems may occur. Korean people, who have lower hair density than western people, have about 100,000 hairs and lose about 50 to about 100 hairs per day, which is a normal phenomenon. Alopecia may be clinically classified into two types: scarring alopecia and non-scarring alopecia. The scarring alopecia involves the destruction of hair follicles and thus hair is not regenerated, whereas the non-scarring alopecia involves the maintenance of hair follicles and thus hair is regenerated after the symptom site disappears. Non-limiting examples of non-cicatricial alopecia, which is non-scarring, include androgenetic alopecia (baldness), alopecia areata, tinea capitis due to fungal infection, telogen effluvium, trichotillomania, and hair growth disorders, and non-limiting examples of cicatricial alopecia, which is scarring, include hair loss due to lupus, folliculitis decalvans, lichen planus pilaris, and alopecia due to burns and trauma. Among these alopecia diseases, the most common diseases are androgenetic alopecia and alopecia areata, and both are non-scarring. Highly frequent hair loss diseases include baldness (male alopecia), female alopecia, alopecia areata, telogen alopecia, and the like. In addition, the alopecia of the present disclosure may further include, in addition to the above-described diseases, all problems due to a loss of many hairs, such as aesthetic problems and the like.

The term "phosphodiesterase (PDE)" as used herein refers to a type of phosphatase which breaks down bonds of phosphodiesters such as cyclic adenosine monophosphate (cAMP), cyclic guanosine monophosphate (cGMP), and the like, and is an enzyme that catalyzes a reaction for generating a phophomonoester and an alcohol through hydrolysis and is classified into a total of 12 subtypes. The PDE regulates the size, location, and persistence of cyclic nucleotide signaling in a cell subdomain, and thus plays a very important role in regulating signaling pathways mediated by several secondary messengers. Since the PDE has unique tissue distribution and unique structural and functional properties, a variety of physiological pathways mediated by cAMP, cGMP, or the like may be affected by inhibiting the hydrolysis of the PDE through inhibition of the PDE, and thus the PDE is currently used as a target for inhibiting various physiological mechanisms and is actively being studied.

The term "phosphodiesterase 3 inhibitor (PDE 3 inhibitor)" as used herein refers to a material that selectively inhibits the subtype III enzyme among phosphodiesterases, and the PDE 3 inhibitor has an excellent effect of enhancing myocardial contraction and excellent vasodilation action and thus is extensively studied as a cardiovascular therapeutic agent. Among the PDE 3 inhibitors, cilostazol, which a quinolinone-based derivative, is one of the PDE 3 inhibitors widely used in the clinical field and increases an intracellular cAMP level in vascular smooth muscle cells which induce vasodilation, and thus is safely used as an antiplatelet drug even for the elderly. In addition, pharmacological and pharmacokinetic properties of the PDE 3 inhibitor are clearly defined, and thus the PDE 3 inhibitor is currently commercially available and widely used for the improvement of ischemic symptoms such as ulcers, pain, coldness, and the like according to chronic total occlusion and the inhibition of recurrence after the onset of a cerebral infarction. In addition, the PDE 3 inhibitor includes, in addition to cilostazol, amrinone (inamrinone), adibendan, anagrelide, benafentrine, bucladesine, carbazeran, cilomilast, cilostamide, enoxamone, fenspiride HCl, 1-cyclopropyl-1-[(1R,2R)-2-hydroxycyclohexyl]-3-[3-[(2-oxo-1H-quinolin-6-yl)oxy]propyl]urea (K-134), 7-[2-[4-(2-chlorophenyl)piperazin-1-yl]ethyl]-1,3-dimethylpurine-2,6-dione (KMUP-1), luteolin, 8-amino-3,7 dihydro-7-(2-methoxyethyl)-1,3-dimethyl-1H-purine-2,6-dione (MKS492), meribendan, milrinone, olprinone, 1-cyclooctyl-1-[(1R,2R)-2-hydroxycyclohexyl]-3-[3-[(2-oxo-1H-quinolin-6-yl)oxy]propyl]urea (OPC-33540), 3-(5,6-dimethoxy-1-benzothiophene-2-yl)-4-methyl-4,5-dihydro-1H-pyridazin-6-one (ORG 9935), parogrelil, pimobendan, pumafentrine, quazinone, 2-[9,10-dimethoxy-4-oxo-2-(2,4,6-trimethylphenyl)imino-6,7-dihydropyrimido[6,1-a]isoquinolin-3-yl]ethylurea (RPL-554), siguazodan, salbutamol, trequinsin, vesnarinone, zardaverine, and the like, and the PDE 3 inhibitor is not particularly limited as long as it is capable of specifically inhibiting the activity of PDE 3.

The term "prevention" as used herein means all actions that inhibit or delay the onset of a disease such as alopecia or the like via administration of the PDE 3 inhibitor according to the present disclosure. The inhibition or delay of the onset of alopecia means all actions including the inhibition of alopecia, i.e., hair loss, the promotion of hair growth (the generation or growth of hair), and a decrease in the development of alopecia due to concurrent occurrence of hair loss inhibition and hair growth promotion.

The term "treatment" as used herein means all actions that improve or beneficially change symptoms of alopecia-associated diseases and the like via administration of the PDE 3 inhibitor according to the present disclosure.

The term "improvement" as used herein means actions that at least reduce parameters related to a condition to be treated, for example, the severity of a symptom. In this regard, the PDE 3 inhibitor of the present disclosure may be simultaneously or separately with or from a drug for the prevention, improvement, or treatment of alopecia.

The term "subject" as used herein refers to an individual to which the PDE 3 inhibitor of the present disclosure may be administered, and the subject is not limited and includes mammals including humans.

In the present specification, the pharmaceutical composition may be in the form of capsules, tablets, granules, an injection, an ointment, powder, or a beverage, and the pharmaceutical composition may be used for humans. The pharmaceutical composition is not limited to the above examples, and may be formulated in the form of oral preparations such as powder, granules, capsules, tablets, an aqueous suspension, and the like, preparations for external application, suppositories, and sterile injection solutions, according to general methods. The pharmaceutical composition of the present disclosure may include a pharmaceutically acceptable carrier. The pharmaceutically acceptable carrier may be a binder, a lubricant, a disintegrant, an excipient, a solubilizing agent, a dispersant, a stabilizer, a suspension agent, a pigment, a flavoring, or the like in the case of oral administration, may be used in combination with a buffer, a preservative, an analgesic agent, a solubilizer, an isotonic agent, a stabilizer, or the like in the case of injections, and may be a base, an excipient, a lubricant, a preservative, or the like in the case of local administration. Preparations of the pharmaceutical composition of the present disclosure may be formulated in a variety of ways by mixing with the above-described pharmaceutically acceptable carrier(s). For example, preparations for oral administration may be formulated in the form of tablets, troches, capsules, elixirs, suspensions, syrups, wafers, or the like, and preparations for injections may be formulated in unit dosage ampoules or in multiple dosage form. In addition, preparations of the pharmaceutical composition may be formulated in the form of solutions, suspensions, tablets, capsules, sustained release type preparations, or the like.

Meanwhile, examples of suitable carriers, excipients and diluents for formulation include lactose, dextrose, sucrose, sorbitol, mannitol, xylitol, erythritol, maltitol, starch, acacia gum, alginates, gelatin, calcium phosphate, calcium silicate, cellulose, methyl cellulose, micro-crystalline cellulose, polyvinylpyrrolidone, water, methylhydroxy benzoate, propylhydroxy benzoate, talc, magnesium stearate, mineral oil, and the like. In addition, the pharmaceutical composition may further include a filler, an anti-coagulant, a lubricant, a wetting agent, a flavoring, an emulsifier, a preservative, or the like.

Administration routes of the pharmaceutical composition according to the present disclosure include, but are not limited to, oral administration, intravenous administration, intramuscular administration, intraarterial administration, intramedullary administration, intradural administration, intracardiac administration, transdermal administration, subcutaneous administration, intraperitoneal administration, intranasal administration, intestinal administration, topical administration, sublingual administration, and rectal administration. The pharmaceutical composition may be administered orally or parenterally. The term "parenteral" as used herein is intended to include subcutaneous, intradermal, intravenous, intramuscular, intraarticular, intrabursal, intrasternal, intradural, intralesional, and intracranial injections or injection techniques. The pharmaceutical composition of the present disclosure may also be administered in the form of a suppository for rectal administration.

The pharmaceutical composition of the present disclosure may vary depending on various factors including the activity of the used specific compound, age, body weight, general health, gender, diet, administration time, administration route, drug combination, and the severity of a particular disease to be prevented or treated, and a dosage of the pharmaceutical composition varies according to the condition and body weight of a patient, the severity of disease, drug form, administration route, and administration period, but may be appropriately selected by one of ordinary skill, and may range from about 0.0001 mg/kg/day to about 50 mg/kg/day or about 0.001 mg/kg/day to about 50 mg/kg/day. The pharmaceutical composition may be administered once or multiple times a day. The dosage is not intended to limit the scope of the present disclosure in any way. The pharmaceutical composition according to the present disclosure may be formulated into pills, dragees, capsules, a liquid, a gel, a syrup, a slurry, or a suspension.

In the present disclosure, the cosmetic composition may include an inhibitor of the advanced glycation end product receptor in an amount of about 0.0005 wt % to about 50 wt % with respect to a total weight of the composition. In addition, the composition of the present disclosure may further include, in addition to the inhibitor of the advanced glycation end product receptor, one or more active ingredients having an identical or similar function.

The cosmetic composition of the present disclosure may be prepared in the form of general emulsified and solubilized preparations, and may be used for humans. A cosmetic prepared using the cosmetic composition of the present disclosure may be prepared in the form of general emulsified and solubilized preparations, the cosmetic for the emulsified preparation may be a nourishing lotion, a cream, an essence, or the like, and the cosmetic for the solubilized preparation may be a skin softener. In addition, the cosmetic may be prepared in the form of an adjuvant which is commonly used in the dermatology field by including a dermatologically acceptable medium or base and may be applied locally or systemically.

Suitable cosmetic preparations may be provided, for example, in the form of a solution, a gel, a solid or pasty anhydrous product, an emulsion obtained by dispersing an oily phase in a water phase, a suspension, a microemulsion, a microcapsule, a microgranule, an ionic (liposomal) or non-ionic vesicle dispersing agent, a cream, a toner, a lotion, a powder, an ointment, a spray, or a conceal stick. In addition, cosmetic preparations may be formulated into the form of a foam, or an aerosol composition further including a compressed propellant.

In addition, the cosmetic composition of the present disclosure may further include an adjuvant commonly used in the cosmetic or dermatological field, such as a fatty material, an organic solvent, a dissolving agent, a concentrating agent, a gelling agent, a softening agent, an antioxidant, a suspending agent, a stabilizer, a foaming agent, an air freshener, a surfactant, water, an ionic or non-ionic emulsifying agent, a filler, metal ion sequestering and chelating agents, a preservative, a vitamin, a blocking agent, a wetting agent, essential oil, a dye, a pigment, a hydrophilic or lipophilic activating agent, a lipid vesicle, or any other component commonly used in cosmetics. In addition, the above ingredients may be introduced in amounts generally used in the dermatological field.

A product to which the cosmetic composition of the present disclosure may be added may be, for example, cosmetics such as an astringent, a skin softener, a nourishing lotion, various creams, an essence, a pack, a foundation, or the like, a cleansing lotion, a face cleansing product, a soap, a treatment agent, a shampoo, an essence, a beauty solution, or the like. Suitable preparations of the cosmetic composition of the present disclosure include a hair tonic, a hair conditioner, a hair essence, a hair lotion, a hair nourishing lotion, a hair shampoo, a hair rinse, a hair treatment, a hair cream, a hair nourishing cream, a hair moisturizing cream, a hair massage cream, a hair wax, a hair aerosol, a hair pack, a hair nourishing pack, a hair soap, a hair cleansing foam, hair oil, a hair drying agent, a hair preservation treatment agent, a hair dye, a hair waving agent, a hair bleaching agent, a hair gel, a hair glaze, a hairdressing agent, a hair lacquer, a hair moisturizer, a hair mousse, a hair spray, a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a press powder, a loose powder, an eye shadow, and the like.

For paste, cream, or gel preparations of the present disclosure, as a carrier ingredient, animal oil, vegetable oil, wax, paraffin, starch, tragacanth, a cellulose derivative, polyethylene glycol, silicon, bentonite, silica, talc, zinc oxide, or the like may be used.

For powder or spray preparations of the present disclosure, lactose, talc, silica, aluminum hydroxide, calcium silicate, or polyamide powder may be used as a carrier ingredient. In particular, in the case of spray preparations, the composition may further include a propellant such as a chlorofluorohydrocarbon, propane/butane, or dimethylether.

For solution or emulsion preparations of the present disclosure, a solvent, a solubilizing agent, or an emulsifying agent may be used as a carrier ingredient, and the carrier ingredient may be, for example, water, ethanol, isopropanol, ethyl carbonate, ethyl acetate, benzyl alcohol, benzyl benzoate, propylene glycol, 1,3-butylglycol oil, a glycerol aliphatic ester, polyethylene glycol, or a sorbitan fatty acid ester.

For suspension preparations of the present disclosure, as a carrier ingredient, a liquid diluent such as water, ethanol, or propylene glycol, a suspension agent such as ethoxylated isostearyl alcohol, polyoxyethylene sorbitol ester, or polyoxyethylene sorbitan ester, micro-crystalline cellulose, aluminum methahydroxide, bentonite, agar, tragacanth, or the like may be used.

For surfactant-containing cleansing preparations of the present disclosure, as a carrier ingredient, an aliphatic alcohol sulfate, an aliphatic alcohol ether sulfate, a sulfosuccinate monoester, isethionate, imidazolinium derivatives, methyltaurate, sarcosinate, fatty acid amide ether sulfate, alkylamidobetaine, an aliphatic alcohol, a fatty acid glyceride, a fatty acid diethanol amide, vegetable oil, a lanolin derivative, an ethoxylated glycerol fatty acid ester, or the like may be used.

The ingredients included in the cosmetic composition of the present disclosure include, in addition to the active ingredient and the carrier ingredient, ingredients commonly used in cosmetic compositions, for example, an antioxidant, a stabilizer, a solubilizer, a vitamin, a pigment, and a flavoring.

The term "quasi-drug" as used herein refers to products used for the purpose of treatment, alleviation, medical care, or prevention of human or animal diseases, or products that have insignificant influences on or do not directly act upon human bodies.

Hereinafter, the following examples will be described to aid in understanding of the present disclosure. However, these examples are provided to more easily understand the present disclosure and are not intended to limit the scope of the present disclosure.

EXAMPLES

Example 1: Induction of Cell Division of Human Hair Follicle-Derived Hair Dermal Papilla Cells (hDPCs) by PDE 3 Inhibitor To evaluate the effect of PDE on the proliferation of hair follicle cells, human hair follicle-derived hDPCs were treated with cilostazol, cilostamide, trequinsin, or milrinone, which are well-known PDE 3 inhibitors, and then subjected to a BrdU assay.

First, primarily cultured hDPCs were treated with cilostazol, cilostamide, trequinsin, or milrinone at a concentration of 0 µM to 10 µM, cultured for 44 hours, treated with a BrdU reagent, and then allowed to react for 4 hours. After culturing for a total of 48 hours, the presence or absence of luminescence was measured using a luminometer for detecting BrdU, and cell division and activation degrees of the hDPCs were identified by comparison with a negative control. The results thereof are shown in Table 1.

As illustrated in FIG. 1, it was confirmed that cilostazol, cilostamide, trequinsin, and milrinone significantly increased the cell division of the hDPCs. From these results, it was confirmed that the PDE 3 inhibitors significantly increased the cell division of hDPCs through inhibition of the activity of PDE 3, and thus could have an effect of promoting hair growth.

Example 2: Identification of Phosphorylation Regulation of Extracellular Signal-Regulated Kinase (ERK) Signaling Protein by PDE 3 Inhibitor in Human Hair Follicle-Derived hDPCs To identify the effects of PDE 3 inhibitors on an ERK signaling pathway, which is a key cell proliferation-associated signaling pathway, human hDPCs were treated with cilostazol, cilostamide, trequinsin, or milrinone at a concentration of 1 µM for 0 minute, 5 minutes, 15 minutes, and 60 minutes, and western blotting was performed thereon. The results thereof are shown in FIG. 2.

Figure 2:
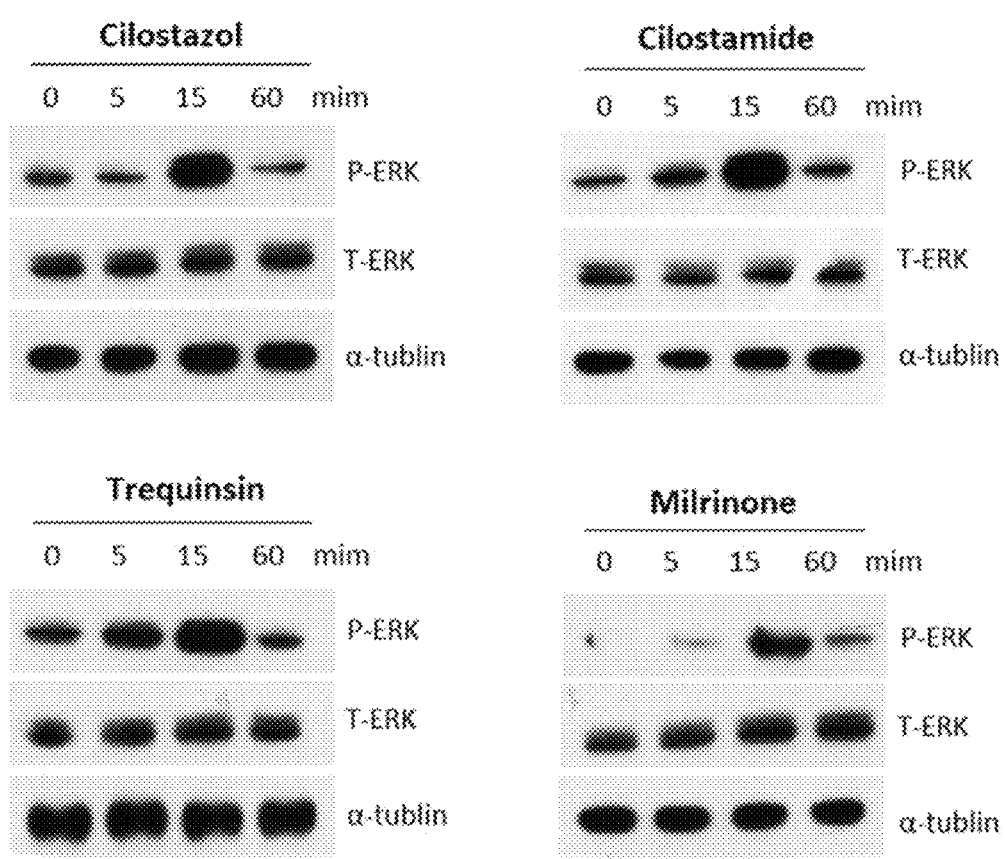
FIG. 2 illustrates western blotting verification results of the effects of PDE 3 inhibitors on cell proliferation-associated signaling pathways, according to an embodiment.

As illustrated in FIG. 2, it was confirmed that the phosphorylation of intracellular ERK proteins was increased by cilostazol, cilostamide, trequinsin, and milrinone within 15 minutes, from which it was confirmed that the PDE 3 inhibitors activated the ERK signaling pathways.

Example 3: Identification of Human Hair Follicle Growth Promotion of PDE 3 Inhibitor Through Ex Vivo Hair Follicle Organ Culture Test To evaluate the effects of PDE 3 inhibitors on human hair follicle growth, an ex vivo hair follicle organic culture test was performed using cilostazol. More particularly, to conduct the ex vivo hair follicle organic culture test, scalp tissues obtained from volunteers were divided into follicular units, and parts below sebaceous glands of the divided hair follicles were cut off and the remaining parts of the hair follicles were used. The prepared hair follicles were cultured in a culture medium containing a negative control reagent or 1 µM or 10 µM cilostazol, the length of hair growing on day 2, day 4, and day 6 was measured, and then a hair growth promotion effect of the human hair follicles was identified by comparison with a negative control. The results thereof are shown in FIG. 3A.

Figure 3A:
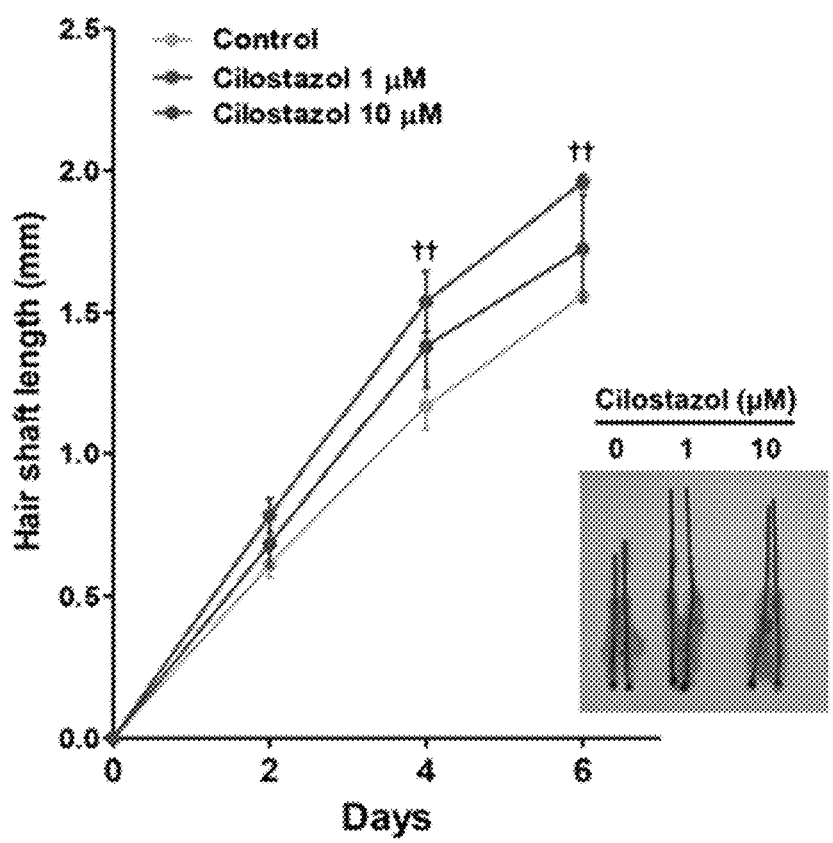
FIG. 3A illustrates a graph and image showing the growth of hair follicles by cilostazol.

As illustrated in FIG. 3A, it was confirmed that cilostazol promoted hair growth of the human hair follicles.

In addition, to identify cell proliferation of the cultured hair follicles through the test, immunofluorescence staining was performed using antibodies against Ki-67, which is a cell division marker. The hair follicles were treated with cilostazol, cultured for two days, and made into a tissue section, the tissue section was cut to a thickness of 4 µm and fixed on a slide, followed by reaction with Ki-67 treated with primary antibodies and treatment with secondary antibodies with green fluorescence capable of detecting Ki-67, and then the resulting section was observed using a fluorescence microscope and photographed, and the number of Ki-67 positive cells was identified. In addition, the nuclei of the hair follicles was stained using a DAPI reagent. The results thereof are shown in FIG. 3B.

Figure 3B:
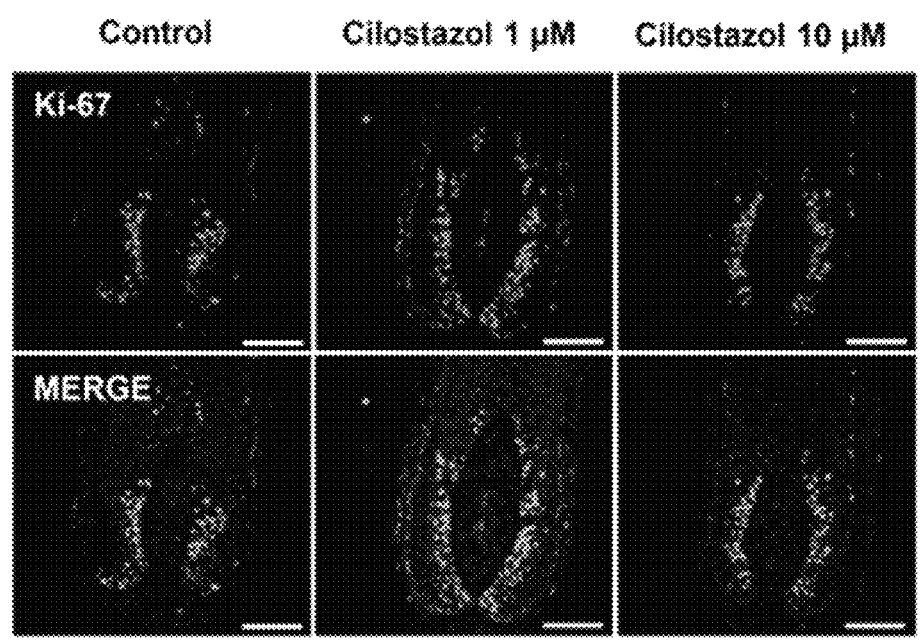
FIG. 3B illustrates images showing results of immunofluorescence staining with Ki-67, which is a cell division marker, to identify cell proliferation in cultured hair follicles.
Figure 3B:
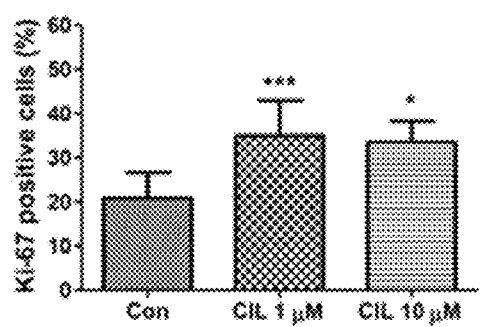

As illustrated in FIG. 3B, it was confirmed that cell division in the human hair follicles was increased by cilostazol.

Example 4: Identification of Hair Growth Anagen Induction Effect by PDE 3 Inhibitor To identify hair growth effects by PDE 3 inhibitors, an anagen induction effect was examined using a C57BL/6 mouse model. Although the hair cycle of human hair varies depending on individuals, mice have the same hair cycle at an initial stage and all hairs enter into a telogen phase 7 weeks to 8 weeks after birth, which then turns into an anagen phase. To evaluate an anagen induction effect using these characteristics of mice, dorsal hairs of 8-week-old C57BL/6 mice in the telogen phase were removed, 0.2 wt % or 1 wt % of cilostazol was applied thereon once a day for three weeks, and then through comparison with a negative control and the case of 2 wt % of minoxidil as a positive control, the presence or absence of hair growth and an anagen induction degree were identified. The results thereof are shown in FIG. 4.

Figure 4:
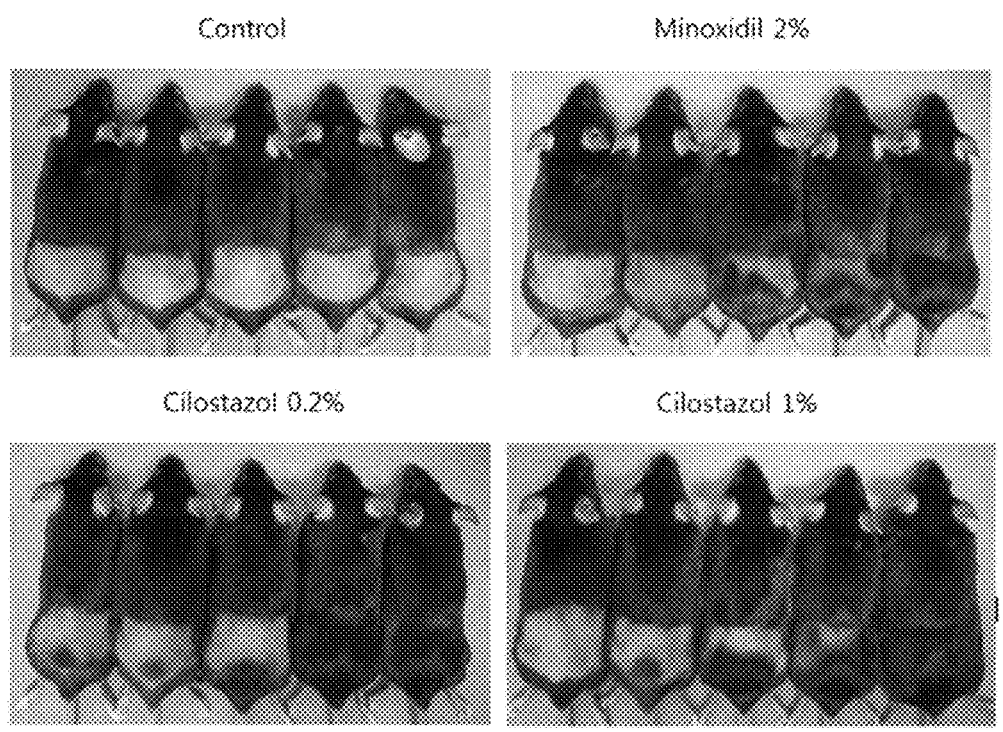
FIG. 4 illustrates verification results of a hair growth degree of a C57BL/6 mouse model treated with cilostazol, according to an embodiment, from which it was confirmed that the anagen phase was induced by cilostazol.

As illustrated in FIG. 4, it was confirmed that the proportion of a site on which anagen hair grew was significantly increased in the cilostazol-treated groups, from which it was confirmed that the PDE 3 inhibitor promoted hair anagen induction.

In addition, skin tissue from which anagen hair grew was fixed with paraffin and stained with hematoxylin and eosin to conduct a histological examination, and the results thereof are shown in FIG. 5.

Figure 5A:
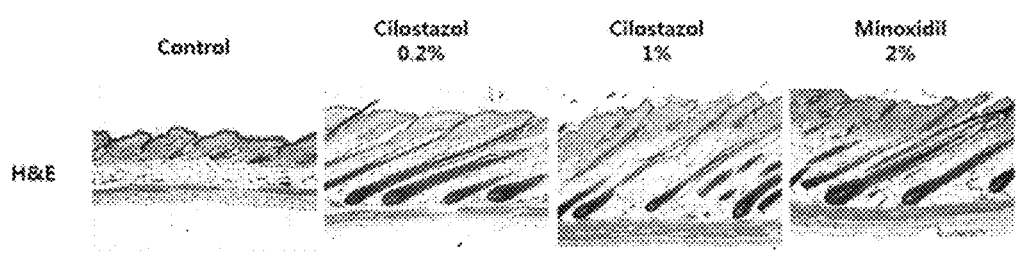
FIG. 5A illustrates histological analysis results of the formation of anagen hair follicles through hematoxylin & eosin staining.
Figure 5B:
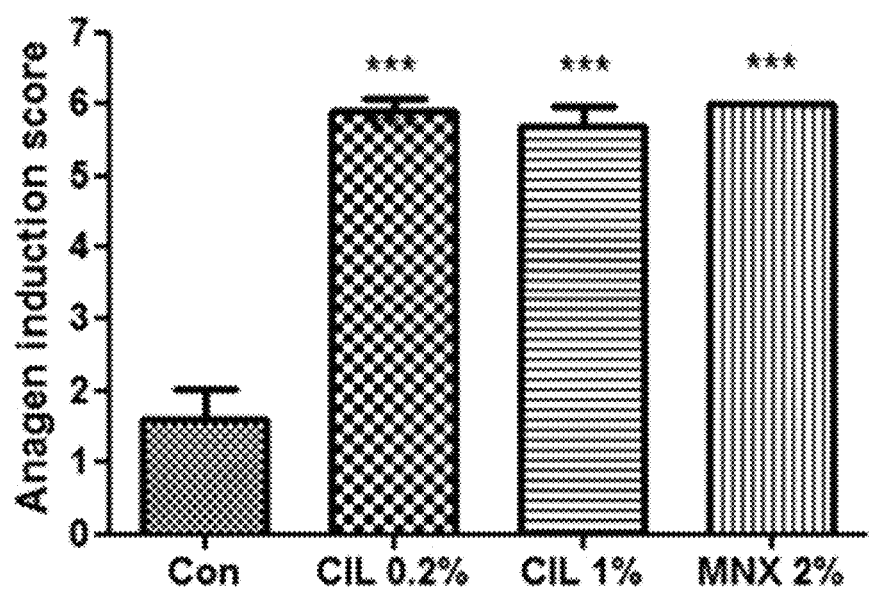
FIG. 5B illustrates identification results of anagen induction scores by cilostazol.
Figure 5C:
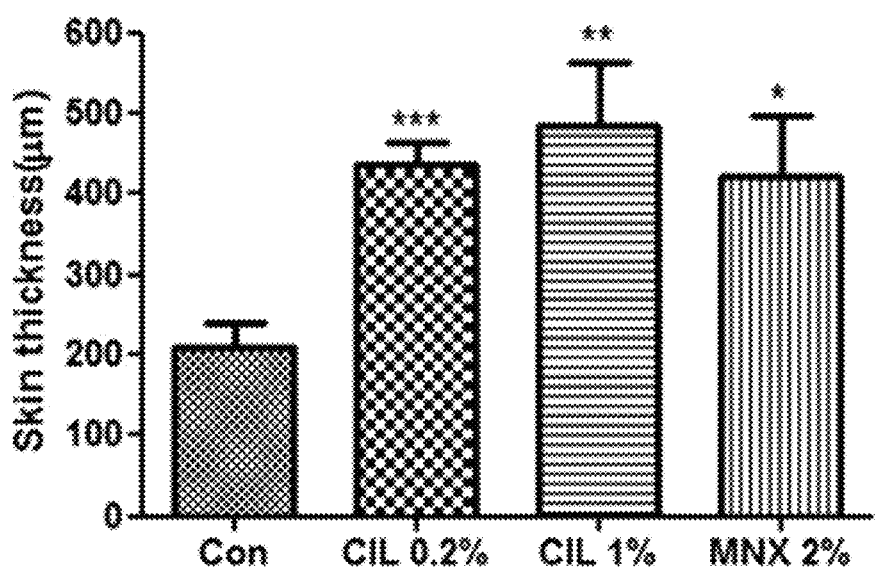
FIG. 5C illustrates identification results of changes in skin thickness by cilostazol.

As illustrated in FIG. 5A, it was confirmed that the formation of hair follicles was promoted in the experimental groups treated with cilostazol, and as illustrated in FIGS. 5B and 5C, increases in anagen induction score and skin thickness were confirmed in the experimental groups treated with cilostazol. In addition, it was confirmed that cilostazol exhibited an effect similar or greater than that of minoxidil even at a concentration of 0.2%, which was lower concentration than that of minoxidil (MNX 2%).

Example 5: Identification of Phosphorylation Regulation of Mitogen-Activated Protein Kinase (MAPK)-Associated Signaling Protein by PDE 3 Inhibitor To verify the effect of a PDE 3 inhibitor on a MAPK-associated signaling pathway, which is a cell proliferation-associated signaling pathway, western blotting was performed using mouse skin tissue. Proteins were extracted from mouse skin tissue of a negative control (Con) and mouse skin tissue on which the anagen induction experiment had been performed by application of cilostazol (CIL) and minoxidil (MNX) as a positive control, certain amounts of the proteins were quantified, and then the phosphorylation of extracellular signal-regulated kinases (ERK), c-Jun N-terminal kinases (JNK), and P-38, which are MAPK-associated proteins, was examined using a western blotting method. The results thereof are shown in FIG. 6.

Figure 6:
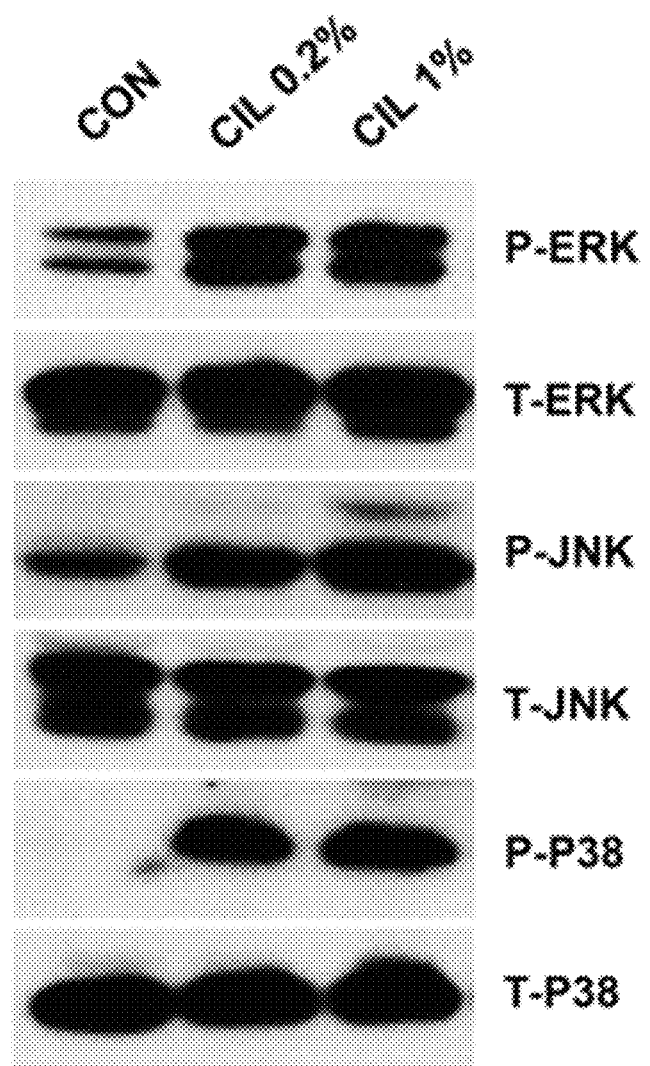
FIG. 6 illustrates verification results of the effect of cilostazol on cell proliferation-associated signaling pathways using mouse skin tissue, according to an embodiment.

As illustrated in FIG. 6, it was confirmed that the phosphorylation of the MAPK-associated signaling proteins was increased by cilostazol.

Example 6: Identification of Angiogenesis Induction by PDE 3 Inhibitor

To verify the effect of a PDE 3 inhibitor on angiogenesis around hair follicles, immunofluorescence staining with CD31, which is a blood vessel marker protein, was performed. More particularly, mouse skin tissue of a negative control and mouse skin tissue on which cilostazol was applied were rapidly cryotreated and prepared into blocks, and then each block was cut into a tissue section having a thickness of 15 µm using a cryotome and immobilized on a slide. In addition, each tissue section was allowed to react with antibodies against CD31, which is a blood vessel marker protein, as primary antibodies, and then treated with secondary antibodies with green fluorescence capable of detecting CD31, and the resulting tissue sections were observed using a fluorescence microscope and photographed, and the area of blood vessels was measured using an image analysis program. The results thereof are shown in FIG. 7.

Figure 7A:
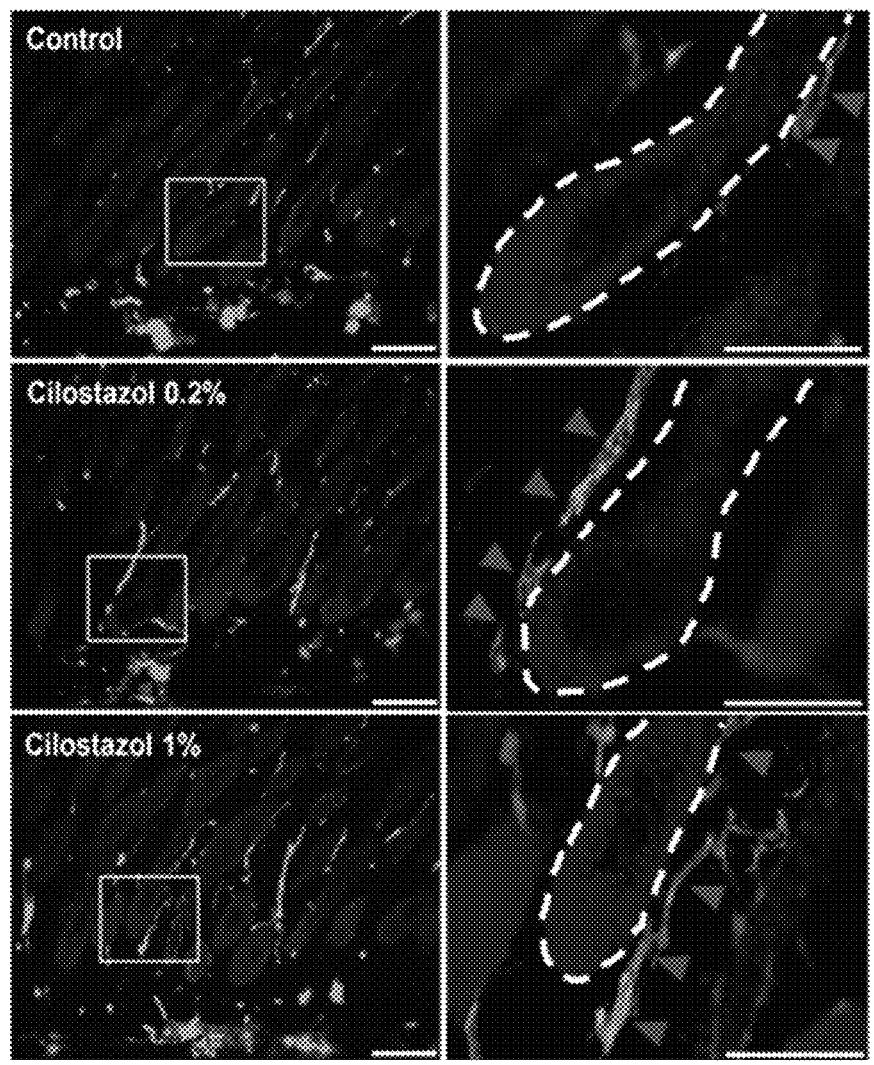
FIG. 7A illustrates results of staining with CD31, which is a blood vessel marker protein.
Figure 7B:
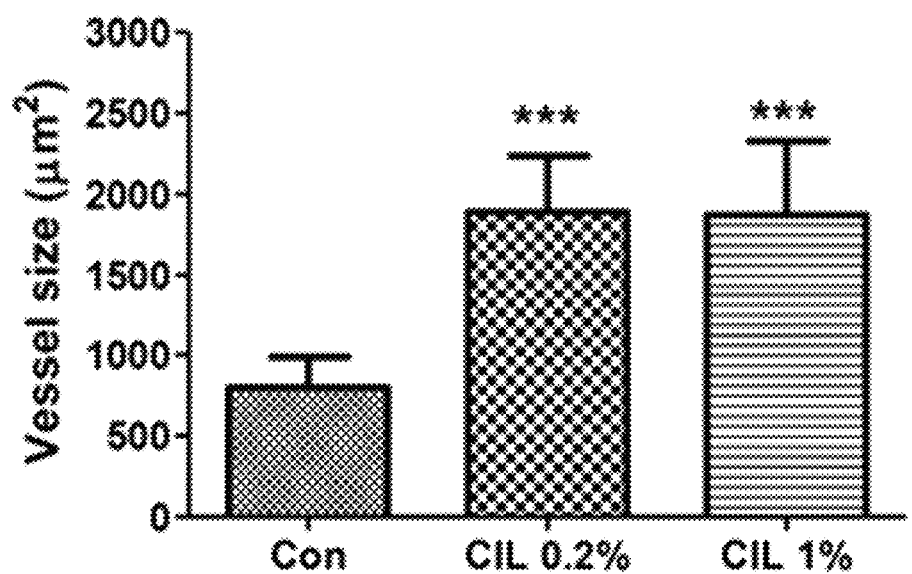
FIG. 7B illustrates vessel size measurement results.

As illustrated in FIG. 7A, it was confirmed that angiogenesis was induced by cilostazol, and as illustrated in FIG. 7B, it was confirmed that the area of blood vessels was also increased.

From the above results, it was confirmed that the PDE 3 inhibitors of the present disclosure activated the ERK proteins and the MAPK-associated signaling proteins by participating in the phosphorylation of these proteins through inhibition of the activity of PDE 3 in the scalp, thus promoting the cell division of hDPDs, angiogenesis, and the like and finally inducing the anagen phase of hair and promoting hair growth, thereby exhibiting a hair growth effect, from which it was confirmed that the PDE 3 inhibitors of the present disclosure prevented or inhibited hair loss or promoted hair growth, and thus could be used for a variety of hair loss-related diseases.

There are various types and plentiful quantities of currently commercially available hair growth-related products, but most products have insignificant or temporary hair loss prevention and hair growth effects, and thus fail to meet the needs of users, and data supporting the efficacy or safety thereof is also insufficient. In addition, even in the case of minoxidil and Propecia proven to have a hair loss prevention effect among these products, it is reported that when the use of these products is stopped, alopecia recurs or severe side effects such as sexual dysfunction, or the like can be caused, and thus the use of these products is considerably limited. Therefore, the inventors of the present disclosure had conducted intensive studies to develop drugs with less side effects and proven to have objective and reproducible effects on alopecia, and as a result, verified that PDE 3 inhibitors had an excellent effect in hair loss prevention or hair growth by promoting hair development through experiments, thus completing the present disclosure. Currently, cilostazol, which is a well-known PDE 3 inhibitor, is used as an antiplatelet agent and pharmacological and pharmacokinetic properties of cilostazol are clearly identified and thus the safety thereof is proven. Thus, when cilostazol is used in developing therapeutic agents for preventing hair loss or promoting hair growth, cosmetics for scalp application, or the like in accordance with the present disclosure, it is expected that since the drug proven to be safe is used, not only cost saving effects can be obtained, but cilostazol can also be more safely applied clinically, as compared to a case in which new drugs are developed.

The foregoing description of the present disclosure is provided for illustrative purposes only, and it will be understood by those of ordinary skill in the art to which the present disclosure pertains that the present disclosure may be easily modified in other particular forms without changing the technical spirit or essential characteristics of the present disclosure. Thus, the above-described embodiments should be construed as being provided for illustrative purposes only and not for purposes of limitation.

What is claimed is:

1. A method of inhibiting hair loss or promoting hair growth comprising administering an effective amount of a phosphodiesterase 3 inhibitor (PDE 3 inhibitor) to a subject in need thereof,
 wherein the PDE 3 inhibitor comprises any one or more selected from the group consisting of, cilostamide and milrinone.

2. The method of claim 1, wherein the PDE 3 inhibitor is administered at a concentration of about 0.0001 mM to about 50 mM.

3. The method of claim 1, wherein the PDE 3 inhibitor promotes the proliferation of human hair dermal papilla cells (hDPCs).

4. A method of treating alopecia comprising administering an effective amount of a phosphodiesterase 3 inhibitor (PDE 3 inhibitor) to a subject in need thereof,
 wherein the PDE 3 inhibitor comprises any one or more selected from the group consisting of, cilostamide and milrinone.

5. The method of claim 4, wherein the alopecia comprises any one or more selected from the group consisting of alopecia areata, androgenetic alopecia, telogen effluvium, traumatic alopecia, trichotillomania, pressure alopecia, anagen effluvium, nasal alopecia, alopecia syphilitica, alopecia seborrheica, symptomatic alopecia, cicatricial alopecia, and congenital alopecia.

* * * * *